(12) United States Patent
Tockman et al.

(10) Patent No.: US 7,674,245 B2
(45) Date of Patent: Mar. 9, 2010

(54) METHOD AND APPARATUS FOR AN ADJUSTABLE SHAPE GUIDE CATHETER

(75) Inventors: Bruce Tockman, Scandia, MN (US); Randy Westlund, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 789 days.

(21) Appl. No.: 09/876,876

(22) Filed: Jun. 7, 2001

(65) Prior Publication Data

US 2002/0188278 A1 Dec. 12, 2002

(51) Int. Cl.
*A61M 5/00* (2006.01)
(52) U.S. Cl. ...................................... 604/171
(58) Field of Classification Search .............. 604/96.01, 604/158–162, 164.01–164.02, 165.01, 165.02, 604/165.03, 523, 525, 530, 534, 527, 528, 604/532, 535
See application file for complete search history.

(56) References Cited

U.S. PATENT DOCUMENTS

| | | | |
|---|---|---|---|
| 4,516,972 A | 5/1985 | Samson | |
| 4,777,951 A | 10/1988 | Cribier et al. | |
| 4,787,884 A * | 11/1988 | Goldberg | 604/8 |
| 4,898,577 A | 2/1990 | Badger et al. | 604/53 |
| 4,976,689 A | 12/1990 | Buchbinder et al. | 604/95 |
| 4,986,814 A * | 1/1991 | Burney et al. | 604/164.11 |
| 5,007,434 A | 4/1991 | Doyle et al. | 128/772 |
| 5,030,204 A | 7/1991 | Badger et al. | 604/95 |
| 5,067,946 A * | 11/1991 | Zhadanov | 604/198 |
| 5,114,414 A | 5/1992 | Buchbinder | 604/95 |
| 5,290,229 A * | 3/1994 | Paskar | 604/95.04 |
| 5,304,131 A * | 4/1994 | Paskar | 604/95.04 |
| 5,318,528 A | 6/1994 | Heaven et al. | |
| 5,376,074 A | 12/1994 | Buchbinder et al. | 604/96 |
| 5,389,090 A | 2/1995 | Fischell et al. | |
| 5,397,304 A | 3/1995 | Truckai | |
| 5,423,772 A | 6/1995 | Lurie et al. | |
| 5,487,757 A | 1/1996 | Truckai et al. | |
| 5,488,960 A | 2/1996 | Toner | |
| 5,497,784 A | 3/1996 | Imran | |
| 5,533,985 A * | 7/1996 | Wang | 604/264 |
| 5,542,938 A * | 8/1996 | Avellanet et al. | 604/528 |
| 5,545,200 A | 8/1996 | West et al. | |
| 5,626,602 A | 5/1997 | Gianotti et al. | 606/198 |
| 5,632,734 A * | 5/1997 | Galel et al. | 604/524 |
| 5,651,785 A | 7/1997 | Abela et al. | 606/15 |
| 5,658,263 A | 8/1997 | Dang et al. | |
| 5,676,653 A | 10/1997 | Taylor et al. | |
| 5,758,562 A | 6/1998 | Thompson | 87/33 |
| 5,775,327 A | 7/1998 | Randolph et al. | |

(Continued)

FOREIGN PATENT DOCUMENTS

DE 3819372 1/1990

(Continued)

*Primary Examiner*—Nicholas D Lucchesi
*Assistant Examiner*—Christopher D Koharski
(74) *Attorney, Agent, or Firm*—Faegre & Benson LLP (57) ABSTRACT

A catheter assembly includes an outer catheter member having a distal flexible end. An inner catheter member is movably disposed within the outer catheter member. Optionally, a handle assembly is coupled with the outer catheter member and the inner catheter member, where the handle assembly is adapted to slide the inner catheter member relative to the outer catheter member.

18 Claims, 7 Drawing Sheets

U.S. PATENT DOCUMENTS

| | | | |
|---|---|---|---|
| 5,782,239 A | 7/1998 | Webster, Jr. | 128/642 |
| 5,814,029 A | 9/1998 | Hassett | |
| 5,868,700 A | 2/1999 | Voda | |
| 5,868,741 A | 2/1999 | Chia et al. | 606/41 |
| 5,882,333 A | 3/1999 | Schaer et al. | |
| 5,902,289 A | 5/1999 | Swartz et al. | |
| 5,911,715 A * | 6/1999 | Berg et al. | 604/525 |
| 5,911,725 A | 6/1999 | Boury | 606/108 |
| 5,935,102 A | 8/1999 | Bowden et al. | 604/95 |
| 5,935,160 A | 8/1999 | Auricchio et al. | |
| 5,984,957 A | 11/1999 | Laptewicz, Jr. et al. | 623/1 |
| 6,021,340 A | 2/2000 | Randolph et al. | |
| 6,066,126 A | 5/2000 | Li et al. | |
| 6,086,548 A | 7/2000 | Chaisson et al. | |
| 6,090,084 A | 7/2000 | Hassett et al. | |
| 6,122,552 A | 9/2000 | Tockman et al. | |
| 6,165,163 A | 12/2000 | Chien et al. | |
| 6,165,167 A | 12/2000 | Delaloye | 604/528 |
| 6,241,726 B1 | 6/2001 | Chia et al. | 606/41 |
| 6,251,104 B1 | 6/2001 | Kesten et al. | |
| 6,277,107 B1 | 8/2001 | Lurie et al. | |
| 6,280,433 B1 | 8/2001 | McIvor et al. | |
| 6,280,456 B1 | 8/2001 | Scribner et al. | 606/192 |
| 6,308,091 B1 | 10/2001 | Avitall | 600/374 |
| 6,322,548 B1 | 11/2001 | Payne et al. | |
| 6,408,214 B1 * | 6/2002 | Williams et al. | 607/122 |
| 6,511,471 B2 | 1/2003 | Rosenman et al. | |
| 6,526,302 B2 | 2/2003 | Hassett | |
| 6,530,914 B1 | 3/2003 | Mickley | |
| 6,537,253 B1 * | 3/2003 | Haindl | 604/158 |
| 6,592,581 B2 | 7/2003 | Bowe | |
| 6,623,449 B2 | 9/2003 | Paskar | |
| 6,638,268 B2 | 10/2003 | Niazi | |
| 6,716,207 B2 | 4/2004 | Farmholtz | |
| 6,755,812 B2 * | 6/2004 | Peterson et al. | 604/528 |
| 6,902,555 B2 | 6/2005 | Paskar | |
| 6,988,570 B2 | 1/2006 | Takeuchi | |
| 7,089,063 B2 | 8/2006 | Lesh et al. | |
| 2001/0005783 A1 | 6/2001 | Hassett | |
| 2001/0039413 A1 | 11/2001 | Bowe | |

FOREIGN PATENT DOCUMENTS

| | | | |
|---|---|---|---|
| JP | 60-21767 | * | 2/1985 |
| WO | WO 99/55412 | | 4/1999 |

* cited by examiner

METHOD AND APPARATUS FOR AN ADJUSTABLE SHAPE GUIDE CATHETER

TECHNICAL FIELD

The present invention relates generally to catheters. More particularly, it pertains to catheters having an adjustable shape for manipulation into complex locations, such as the coronary sinus ostium.

BACKGROUND

Current cardiac treatments employing the use of catheters are dependent upon complexity of the location to be treated, unless surgery is employed to access complex locations. The physician has had to choose between placing the catheter and treating a site in a place of greatest interest or areas which are anatomically accessible with catheters. Prior catheter placement has been generally restricted to areas which can be repeatedly accessed by the physician. One approach to expand the areas in which a catheter can be placed includes the use of steerable catheter. One type of steerable catheter offers maneuverability to specific, otherwise inaccessible sites by providing catheters shaped specifically to access a particular site. This type of catheter is limited as it cannot be used to reach locations requiring active articulation during placement.

Other types of steerable catheters provide catheters having deflecting tips, which include a pullwire attached to the distal tip portion of the catheter. During use of this type of catheter, the wire is pulled causing the tip to defect. Alternatively, the wire is restrained while the catheter is advanced, allowing the distal tip to deflect. However, one drawback is that the tip of the catheter is deflected only in a prescribed manner. While the tip can be altered during the placement of the catheter, the steerable tip has a radius of curvature which is fixed, thus restricting the accessibility of the distal tip to certain anatomical sites. This results in a limit to the complexity of the site in which the catheter can be positioned.

Another drawback is that an inventory of different sized catheters is necessary, where each catheter has a differently sized radius of curvature. In addition, it is occasionally not known what size of radius is appropriate prior to procedure. When it is discovered, after the catheter has been positioned, that the radius of the catheter is incorrect, the catheter must be completely withdrawn from the patient, and a new properly radiused catheter tip must be reintroduced into the heart. This substitution can cause additional trauma to the patient, and is costly since it adds time to the procedure. In addition, the initially selected but improperly sized catheter must then be discarded, never having been used for its intended purpose. This adds more unnecessary cost since the catheters are typically single use items which are discarded after a single use.

Accordingly, what is needed is a catheter which is adjustable, and which can be positioned within complex locations of a body and is able to accommodate a variety of anatomical variations. What is further needed is a catheter having a shape which is modifiable during a procedure.

SUMMARY

A catheter assembly has an outer catheter member which extends from a first distal end to a first proximal end, where the first distal end is flexible. The outer catheter member includes a first lumen therein, where the first lumen extends from the first distal end to the first proximal end. An inner catheter member is movably disposed within the first lumen of the outer catheter member. The inner catheter member extends from a second distal end to a second proximal end.

Options which can be included with that above are as follows. For instance, a braid of material is disposed within a wall of the outer catheter member and/or the inner catheter member, or between the outer and inner catheter members. In addition, the outer catheter member is defined in part by a first length from the first distal end to the first proximal end, the braid defined in part by a second length, and the second length of the braid is less than the first length. Another example of an option includes having the first distal end of the outer catheter member including two or more segments of material, such as a first segment and a second segment, and the first segment comprises a different material than the second segment.

A further option is where the first distal end of the outer catheter member includes two or more segments of material, including a first segment and a second segment, and the first segment has a different durometer than the second segment. Yet another option includes the outer catheter member having a preformed curve proximate to the first distal end. Optionally the inner catheter member has a preformed curve proximate to the second distal end. Another option is where the outer catheter member is more flexible than the inner catheter member. A further embodiment includes a handle adapted to slide the inner catheter member relative to the outer catheter member.

In another embodiment, a catheter assembly has an outer catheter member which extends from a first distal end to a first proximal end, where the first distal end is flexible. The outer catheter member includes a first lumen therein, where the first lumen extends from the first distal end to the first proximal end. An inner catheter member is movably disposed within the first lumen of the outer catheter member. The inner catheter member extends from a second distal end to a second proximal end. The catheter assembly includes a handle assembly having an outer handle member and an inner handle member, where the inner handle member is slidably received within the outer handle member. The outer catheter member is coupled with the first proximal end of the outer handle member, and the inner catheter member is coupled with the second proximal end of the inner handle member.

Options which can be included with that above are as follows. For instance, one option includes the outer handle member having a cut out therein, and the inner handle member has a projection, where the projection is slidingly disposed through the cut out. Another option is where the outer catheter member is more flexible than the inner catheter member. Another example of an option includes having the first distal end of the outer catheter member including two or more segments of material, such as a first segment and a second segment, and the first segment comprises a different material than the second segment.

A further option is where the first distal end of the outer catheter member includes two or more segments of material, including a first segment and a second segment, and the first segment has a different durometer than the second segment. Yet another option includes the outer catheter member having a preformed cur e proximate to the first distal end. Optionally the inner catheter member has a preformed curve proximate to the second distal end. In another option, a braid of material is disposed within a wall of the outer catheter member and/or the inner catheter member, or between the outer and inner catheter members. Yet another option includes a luer hub adapted to secure the outer catheter member with the outer handle member. In yet another option, the assembly further includes a sprocket having sprocket teeth which are movably coupled with the outer hand e member. In addition, the inner handle member includes inner member teeth which are engaged which the sprocket teeth of the outer handle member.

A catheter assembly has an outer catheter member which extends from a first distal end to a first proximal end. The outer catheter member includes a first lumen therein, where the first lumen extends from the first distal end to the first proximal end. An inner catheter member is movably disposed within the first lumen of the outer catheter member. The inner catheter member extends from a second distal end to a second proximal end, where the inner catheter member has a second lumen therein. The second lumen of the inner catheter member extends from the second distal end to the second proximal end. In addition, a means for flexing the first distal end of the outer catheter member is included. Options include those discussed above.

A method includes disposing an inner catheter member within an outer catheter member, where the outer catheter member extends from a first distal end to a first proximal end, and the first distal end is flexible. The outer catheter member has a first lumen, and the inner catheter member has a second lumen therein. The method further includes inserting the outer catheter member and the inner catheter member within a body, moving the inner catheter member relative to the outer catheter member, and flexing the first distal end of the outer catheter member.

Options for the method are as follows. The method optionally further includes disposing fluid and/or a medical device through the second lumen of the inner catheter member. A further option includes removing the inner catheter member. Yet another option includes disposing fluid and/or a medical device through the first lumen of the outer catheter member before or after the inner catheter has been removed. In addition, optionally torque is applied to the inner catheter member. A further option includes sliding the inner catheter member within the outer catheter member.

The catheter assembly is easily manipulatable by the physician into complex shapes, which allows for the assembly to be positioned into complex areas within a patient, for instance, within the coronary sinus ostium. Since the catheter assembly is able to be positioned within many different areas, regardless of their complexity in shape, a physician has more available options when treating a patient. A her benefit of the catheter assembly is that the device is easy to use, easy to manufacture, and provides a cost benefit in both assembly and in its use.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiment may be utilized and that structural changes may be made without departing from the scope of the present invention. Therefore, the following detailed description is not to be taken in a limiting sense, and the scope of the present invention is defined by the appended claims and their equivalents.

Figure 1:
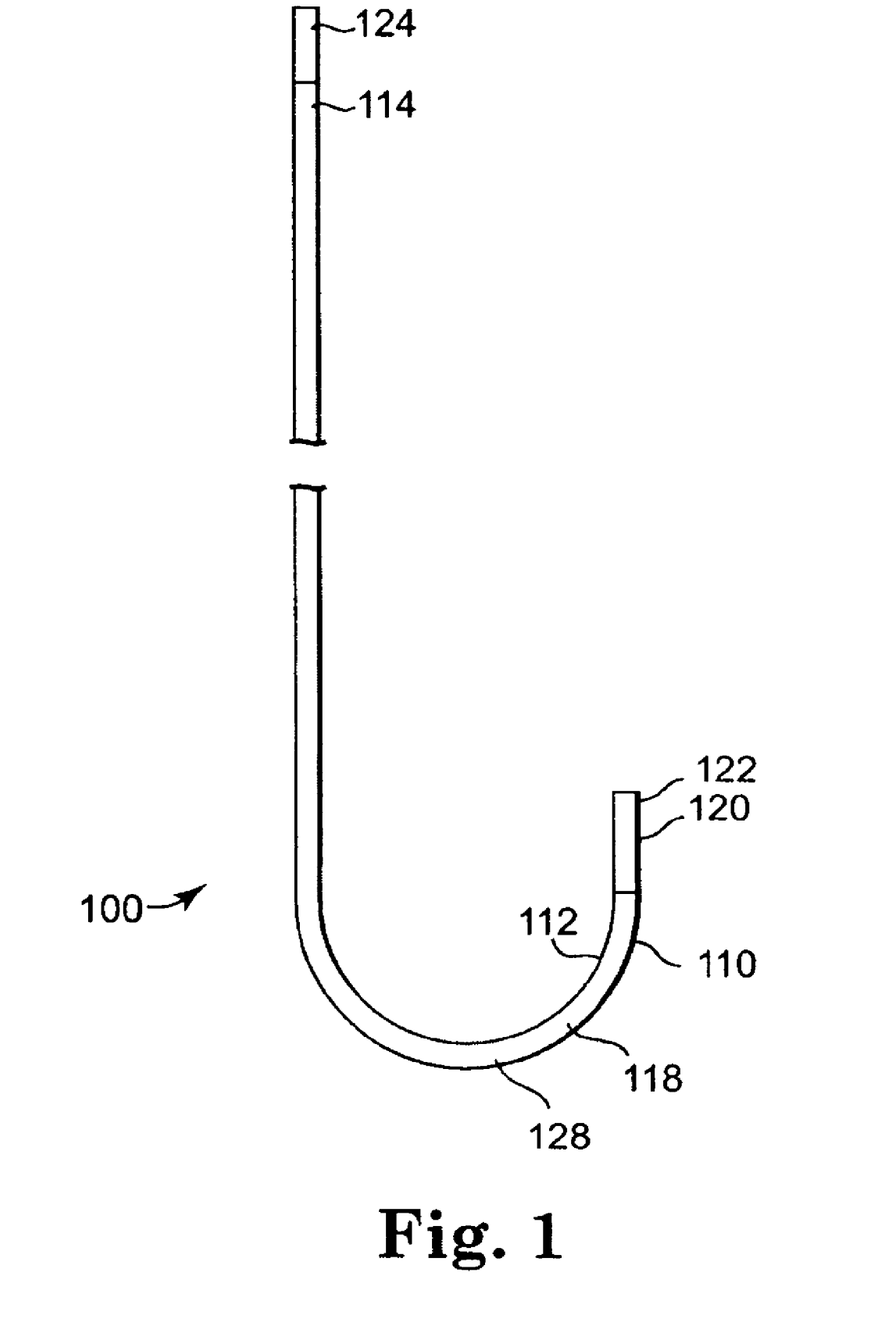
FIG. 1 is a side elevational view illustrating a catheter assembly constructed in accordance with one embodiment.
Figure 2:
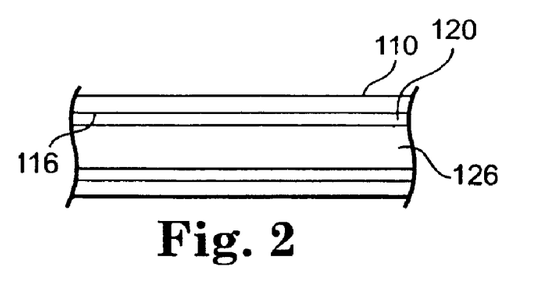
FIG. 2 is a cross sectional view illustrating a catheter assembly constructed in accordance with one embodiment.
Figure 3:
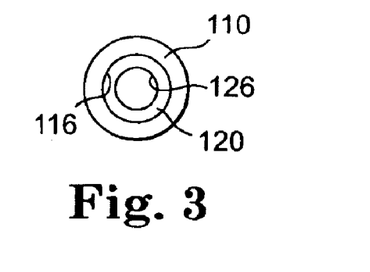
FIG. 3 is a cross sectional view illustrating a catheter assembly constructed in accordance with one embodiment.

A catheter having an adjustable shape is provided. The adjustable catheter is used for cannulating complex locations within a body, for instance, within the coronary sinus ostium for the purpose of acute deployment of drugs or acute and chronic deployment of medical instrumentation or devices such as a pacing lead. FIG. 1 illustrates a catheter assembly 100 constructed in accordance with one embodiment. The catheter assembly generally includes an outer catheter member 110 and an inner catheter member 120 which is movably received by the outer catheter member 110. The outer catheter member 110 extends from a first distal end 112 to a first proximal end 114, and has a first lumen 116 therein, as shown in FIGS. 2 and 3. The first lumen 116 extends from the first distal end 112 to the first proximal end 114 of the outer catheter member 110. The first distal end 112 of the outer catheter member 110 is flexible. Optionally, the entire outer catheter member 110 is more flexible than the inner catheter member 120. In one embodiment, the first distal end 112 of the outer catheter member 110 has a preformed curve 118 therein.

The first lumen 116 of the outer catheter member 110 receives therein the inner catheter member 120. The inner catheter member 120 extends from a second distal end 122 to a first proximal end 124, and optionally has a second lumen 126 therein, as shown in FIGS. 2 and 3. The second lumen 126 extends from the second distal end 122 to the second proximal end 124 of the inner catheter member 120. In another option, the inner catheter member 120 does not have a lumen, such as an electrode catheter. The user optionally can open the hemostasis mechanism, discussed further below, and extend the electrode catheter out of the outer catheter member to use the electrodes thereon to sense and/or pace tissue.

In one option, the inner catheter member 120 has a preformed curve 128 therein. The preformed curve 128 of the inner catheter member 120 is provided in addition to the preformed curve 118 of the outer catheter member 110. Alternatively, the preformed curve 128 of the inner catheter member 120 is provided in alternative to the preformed curve 118 of the outer catheter member 110.

Figure 4:
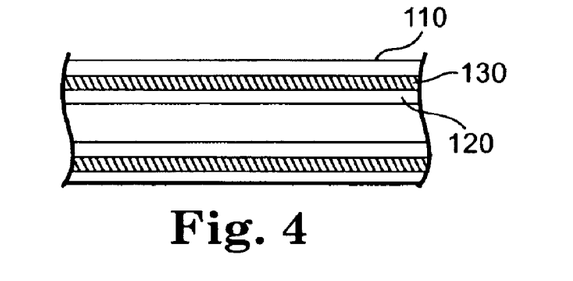
FIG. 4 is a cross sectional view illustrating a catheter assembly constructed in accordance with one embodiment.
Figure 5:
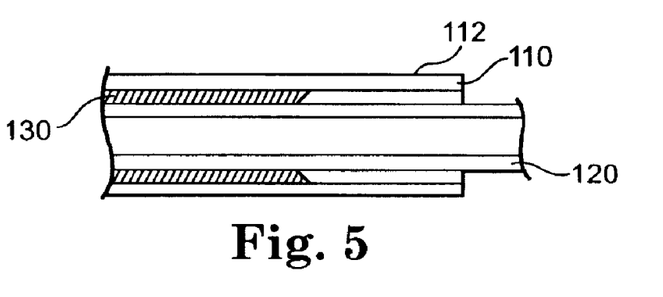
FIG. 5 is a cross sectional view illustrating a catheter assembly constructed in accordance with one embodiment.
Figure 6:
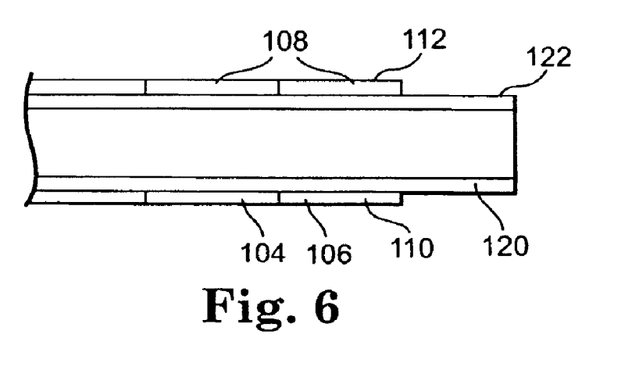
FIG. 6 is a cross sectional view illustrating a catheter assembly constructed in accordance with another embodiment.

FIGS. 4-6 illustrate other options for the catheter assembly 100. In one option, the catheter assembly 100 includes a braid 130 of material, where the braid 130 is disposed between the outer catheter member 110 and the inner catheter member 120, as shown in FIG. 4. Optionally, the braid 130 of material is secured to the inner catheter member 120 or the outer catheter member 110, for example by providing the braid 130 of material within the wall construction of the inner and/or outer catheter member. It should be noted that providing the braid 130 of material within the wall construction also includes, but is not limited to, forming the braid in the center of the wall, the outer portion of the wall, or the inner portion of the wall of the inner or outer catheter member. In yet another option, the inner catheter member 120 is releasably attached to the inner handle, using a luer style hub. The braid 130 of material includes a braid 130 of stainless steel material, although sleeves of other types of materials would be suitable as well, such as flat or round wire, rigid polymeric material such as PTFE, polyurethane, or polyesters. In one embodiment, the braid 130 of material has a length which is less than that of the outer catheter member 110, as shown in FIG. 5.

FIG. 6 illustrates another embodiment of the catheter assembly 100, where the first distal end 112 of the outer catheter member 110 includes two or more segments 108 of material. The two or more segments include, but are not limited to, a first segment 104 and a second segment 106. In one option, the first segment 104 is comprised of a different material than the second segment 106 In another option, the first segment 104 is comprised of a material having a different durometer than the material of the second segment 106.

Figure 7:
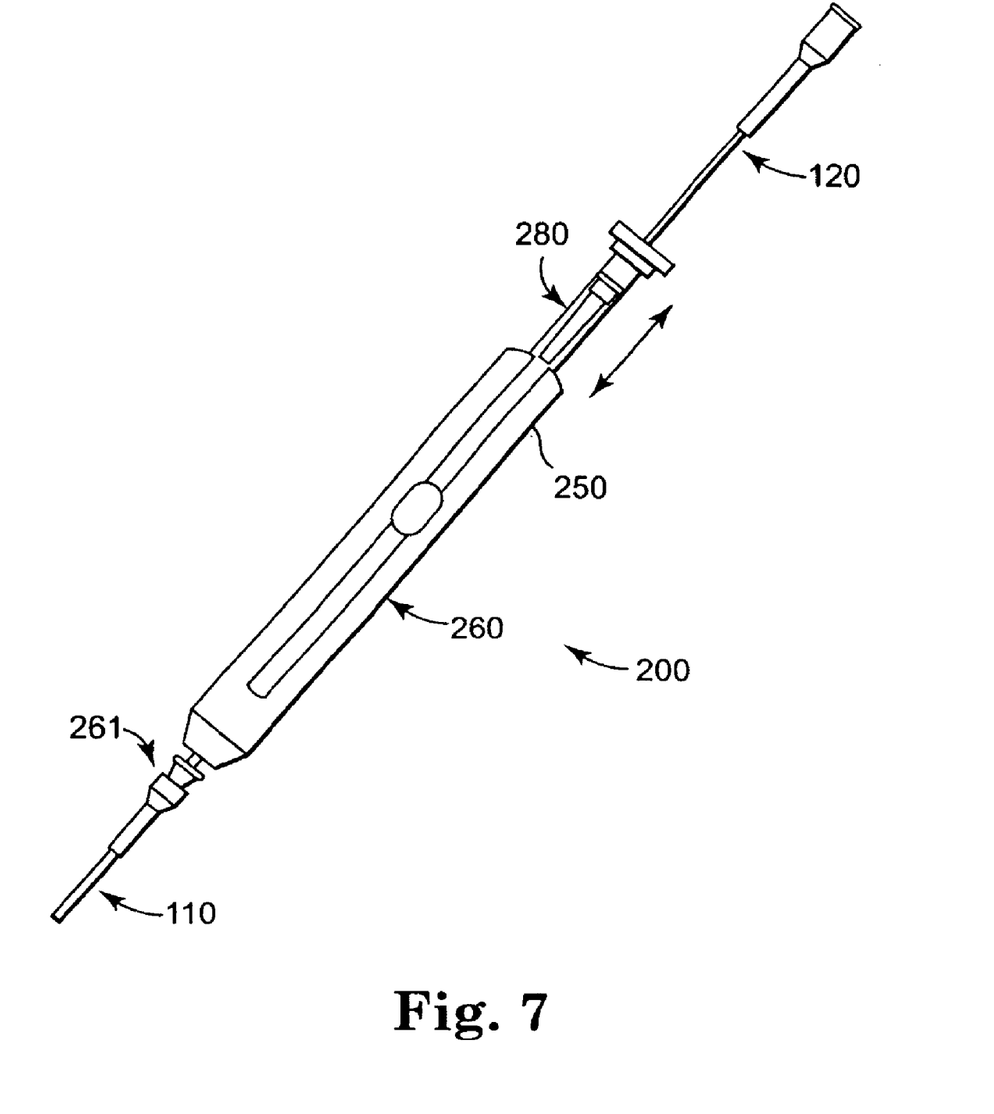
FIG. 7 is a side elevational view illustrating a catheter assembly constructed in accordance with one embodiment.

FIG. 7 illustrates another embodiment of a catheter assembly 200. The catheter assembly 200 includes the outer catheter member 110 and the inner catheter member 120, and the variations thereto, as discussed above in reference to FIGS. 1-6. In addition, the catheter assembly 200 includes a handle assembly 250 which is adapted to move the inner catheter member 120 relative to the outer catheter member 110.

Figure 8:
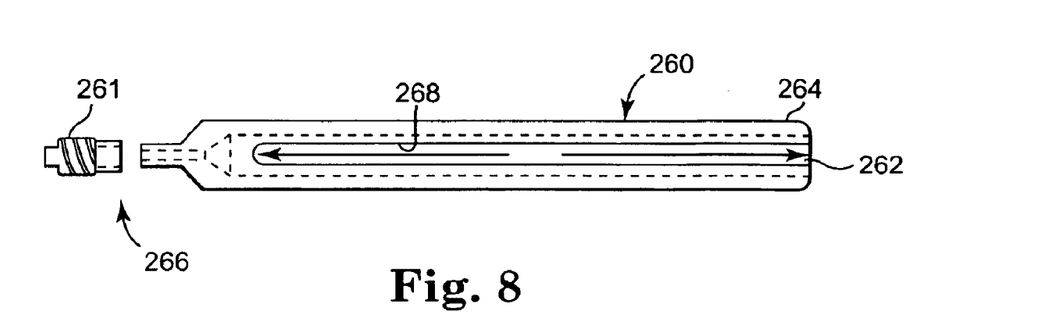
FIG. 8 is a side elevational view illustrating an outer handle member of a catheter assembly constructed in accordance with one embodiment.
Figure 9:
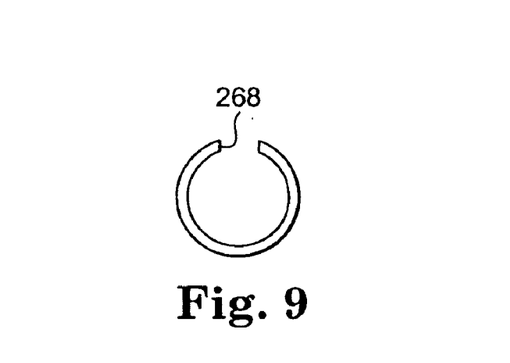
FIG. 9 is a cross sectional view illustrating an outer handle member of a catheter assembly constructed in accordance with one embodiment.

The handle assembly 250 includes an outer handle member 260 and an inner handle member 280. The inner handle member 280 is slidably received by the outer handle member 260. The outer handle member 260, as shown in more detail in FIGS. 8 and 9, has a first passage 262 for receiving the inner handle member 280 therein. The first passage 262 extends from a distal end 266 to a proximal end 264 of the outer handle member 260, and allows for fluids and/or instrumentation to be disposed therethrough. The outer handle member 260 further includes a cut out 268 therein, which optionally, extends only partially from the distal end 266 to the proximal end 264. The cut out 268, as shown in cross-section in FIG. 9, is adapted to receive therethrough a portion of the inner handle member 280, as discussed further below. Referring again to FIG. 7, the outer handle member 260 is coupled with the outer catheter member 110, and is optionally coupled with a luer style hub 261.

Figure 10:
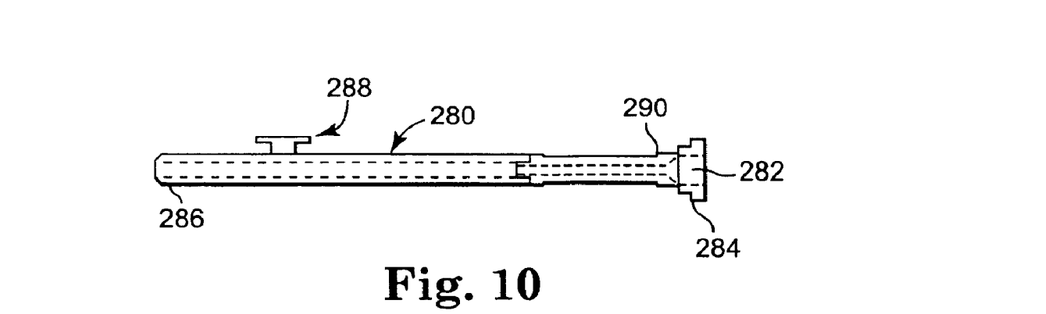
FIG. 10 is a side elevational view illustrating an inner handle member of a catheter assembly constructed in accordance with one embodiment.

The inner handle member 280 is shown in more detail in FIG. 10. The inner handle member 280 includes an inner passage 282 therein. The inner passage 282 extends from a distal end 286 to a proximal end 284 of the inner handle member 280, and allows for fluids and/or instrumentation to be disposed therethrough. The inner handle member 280 further includes a projection 288. The projection 288 is optionally integral with the inner handle member 280. Alternatively, the projection 288 is a separate component which is coupled with the inner handle member 280.

The inner handle member 280 is coupled with the inner catheter member 120, in one embodiment, with an adjustable grommet and hub mechanism, for instance, a hemostasis-like mechanism 290. The hemostasis-like mechanism 290 allows for different inner catheter members to be interchanged within the catheter assembly 200. For instance, inner catheter members having differing amounts of stiffness and/or varying shapes can be used to achieve further complex movements through the vasculature.

As a user advances the projection 288 which is slidingly received in the cut out 268, for example, by using a thumb, the inner catheter member 120 is moved within the outer catheter member 110, thereby altering the distal end 112 of the outer catheter member 110. As the distal end 112 of the outer catheter member 110 is modified, a change results in the curve of the distal end 112 to modify the geometry and the position of the catheter assembly 200.

Figure 11:
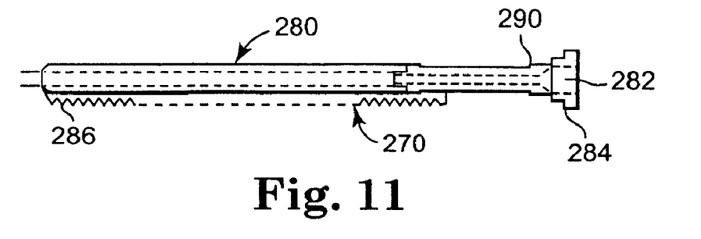
FIG. 11 is a side elevational view illustrating an inner handle member of a catheter assembly constructed in accordance with one embodiment.
Figure 12:
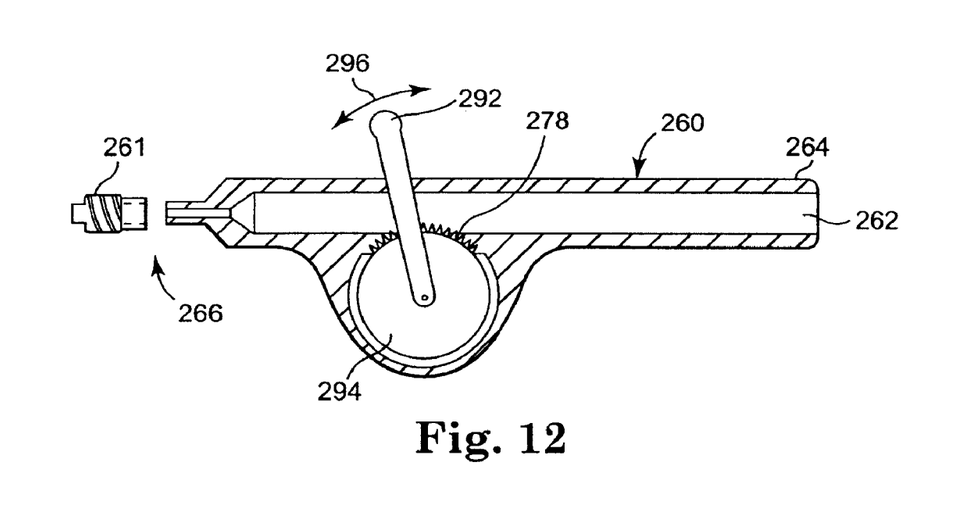
FIG. 12 is a side elevational view illustrating an outer handle member of a catheter assembly constructed in accordance with one embodiment.
Figure 13:
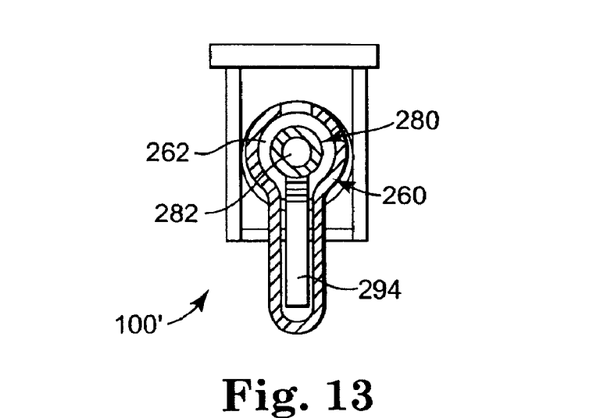
FIG. 13 is a cross sectional view illustrating an outer handle member of a catheter assembly constructed in accordance with one embodiment.

FIGS. 11-13 illustrate another embodiment of the catheter assembly 100'. Similar to the previously discussed embodiment, the handle assembly 250 includes an outer handle member 260 and an inner handle member 280. The inner handle member 280 is slidably received by the outer handle member 260. The outer handle member 260, as shown in more detail in FIGS. 12 and 13 has a first passage 262 for receiving the inner handle member 280 therein. The first passage 262 extends from a distal end 266 to a proximal end 264 of the outer handle member 260, and allows for fluids and/or instrumentation to be disposed therethrough.

The outer handle member 260 further includes a sprocket 294 movably coupled with the outer handle member 260. For instance, in one option, the sprocket 294 is rotatably coupled with the outer handle member 260. The sprocket 294 includes a lever 292 which allows for the sprocket to be rotated along 296. It should be noted that the lever 292 is usable to implement other motions of movement, such as linear movement. The sprocket 294 further includes sprocket teeth 278, which are configured to engage with a portion of the inner handle member 280, as further discussed below.

The inner handle member 280 is shown in more detail in FIG. 11. The inner handle member 280 includes an inner passage 282 therein. The inner passage 282 extends from a distal end 286 to a proximal end 284 of the inner handle member 280, and allows for fluids and/or instrumentation to be disposed therethrough. The inner handle member 280 further includes inner member teeth 270 projecting from a surface of the inner handle member 280. The inner member teeth 270 are configured to engage the sprocket teeth 278. As a user manipulates the sprocket 294, for example by using the lever 292, the inner handle member 280 is moved relative to the outer handle member 260. As the sprocket teeth 278 engage the inner member teeth 270, the inner catheter member 120 (FIG. 7) is moved within the outer catheter member 110 (FIG. 7), thereby altering the distal end 112 (FIG. 1) of the outer catheter member 110 (FIG. 7). As the distal end 112 (FIG. 1)

of the outer catheter member 110 (FIG. 7) is modified, a change results in the curve of the distal end 112 (FIG. 1) to modify the geometry and the position of the catheter assembly 200 (FIG. 7). The sprocket 294 and the lever 292 facilitates single-handed manipulation of the instrument, freeing the physicians other hand for other types of catheter manipulation or for manipulation of other medical instruments.

During use of the catheter assembly, a method includes disposing an inner catheter member within an outer catheter member, to form one of the several catheter assemblies discussed above, where the outer catheter member extends, from a first distal end to a first proximal end, and the first distal end is flexible. As mentioned above, the outer catheter member has a first lumen, and the inner catheter member has a second lumen. The inner catheter member is disposed within the first lumen of the outer catheter member.

Figure 14:
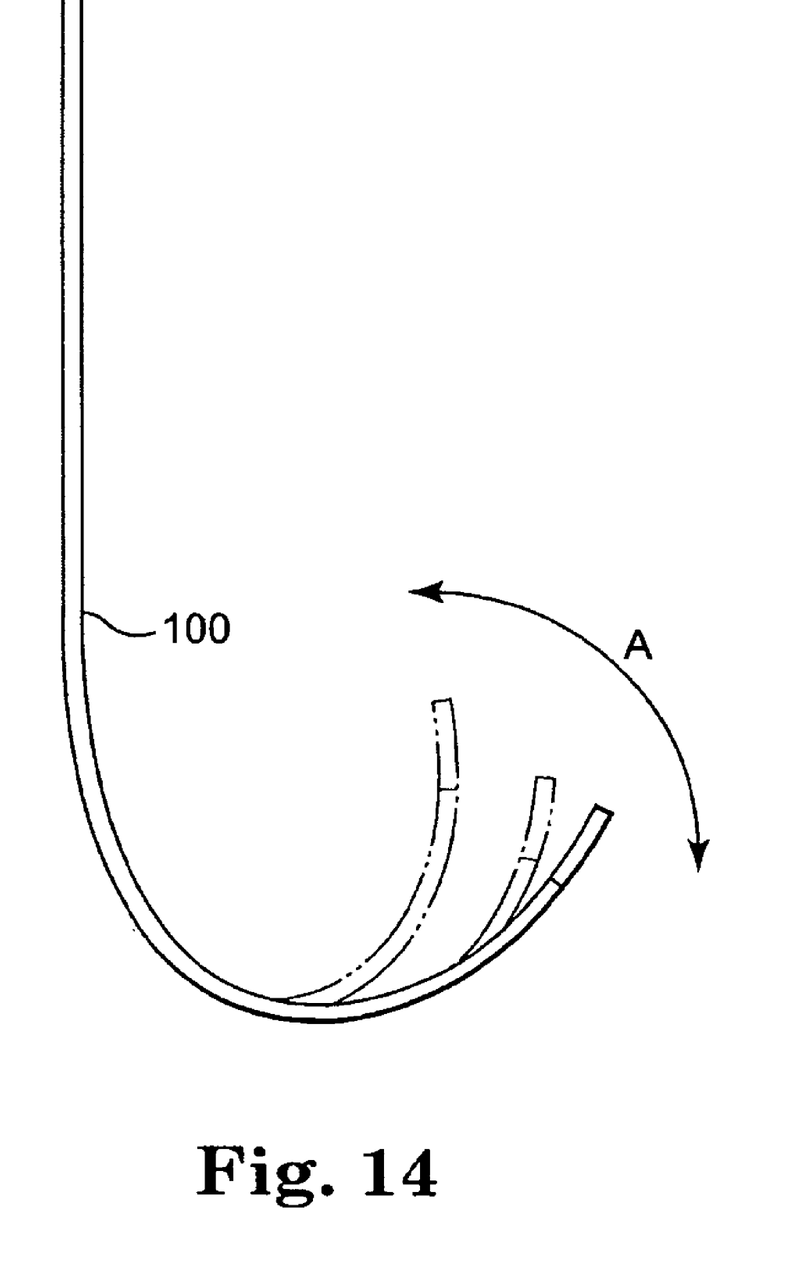
FIG. 14 is a side elevational view illustrating a catheter assembly constructed in accordance with one embodiment.
Figure 15:
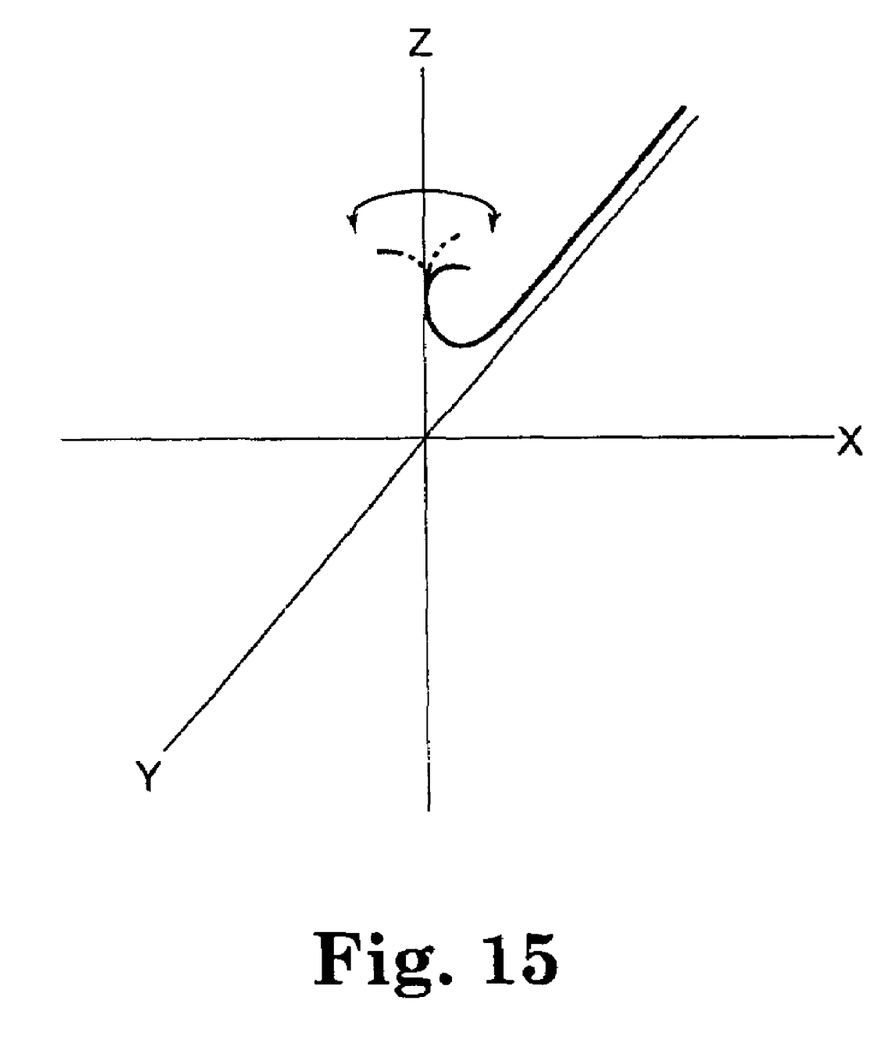
FIG. 15 is a view illustrating a catheter assembly constructed in accordance with one embodiment.

The method further includes inserting the outer catheter member and the inner catheter member within a body, for instance, of a human patient. The inner catheter member is moved relative to the outer catheter member, for instance, by sliding the inner catheter member within the outer catheter member. Optionally, as discussed above, a handle assembly is used to slide the inner catheter member relative to the outer catheter member. The first distal end of the outer catheter member, in one option, is flexed in a two dimensional motion as shown in FIG. 14 along "A." In another option, as shown in FIG. 15, the first distal end of the outer catheter member is flexed in a three dimensional motion, for example, by rotating the shaped inner catheter member. Flexing of the outer catheter member allows positioning of the catheter assembly within complex locations of a patient.

Once the catheter assembly is positioned within the body, or at least partially positioned within the body, fluid and/or a medical device is disposed through the second lumen of the inner catheter member. The medical device, for example, comprises a cardiac lead or alternatively, a guidewire. The fluid includes, but is not limited to, saline or medicine, or radiopaque dye. Optionally, the inner catheter member is removed from the catheter assembly, and fluid and/or a medical device is disposed through the first lumen of the outer catheter member. The implanting physician or technician has more options since the various lumens accommodate various types and sizes of medical instruments, or rates of introduction of fluids. In yet a further option, torque is applied to the inner catheter member, which is particularly beneficial, for instance, when the inner catheter is shaped in conjunction with the outer catheter. Applying torque to the inner catheter having a preformed shape provides a three-dimensional geometry at the tip. In yet another option, a stiff guide wire, either straight or preformed, is advanced down the central lumen of the inner catheter, which allows for additional shape control.

Advantageously, the catheter assembly is easily manipulatable by the medical technician into complex shapes, which allows for the assembly to be positioned in to complex areas within a patient, for instance, within the coronary sinus ostium. Since the catheter assembly is able to be positioned within many different areas, regardless of their complexity in shape, a medical technician or physician has more available options when treating a patient. A further benefit of the catheter assembly is that the device is easy to use, easy to manufacture, and provides a cost benefit in both assembly and in its use.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present invention. The scope of the invention should, therefore, be determined with reference to the appended claims, along with the full scope of equivalents to which such claims are entitled.

What is claimed is:

1. A catheter assembly comprising:
    an outer catheter member extending from a first distal end to a first proximal end, where the first distal end is flexible and comprises regions of varying stiffness, and has a pre-formed curvature;
    the outer catheter member having a first lumen therein, the first lumen extending from the first distal end to the first proximal end, the outer catheter member further including an outer handle member coupled to the first proximal end;
    a flexible inner catheter member movably disposed within the first lumen of the outer catheter member;
    the inner catheter member extending from a second distal end to a second proximal end and including an inner handle member coupled to the second proximal end, the second distal end having a pre-formed curvature; and
    the outer catheter member is more flexible than the inner catheter member,
    wherein the outer and inner catheter members are configured such that relative translation and rotation of the outer and inner catheter members causes the first distal end of the outer catheter member to assume a plurality of two and three dimensional shapes.

2. The catheter assembly as recited in claim 1, further comprising a braid of material disposed between the outer catheter member and the inner catheter member.

3. The catheter assembly as recited in claim 2, wherein the outer catheter member is defined in part by a first length from the first distal end to the first proximal end, the braid defined in part by a second length, and the second length is less than the first length.

4. The catheter assembly as recited in claim 1, further comprising a braid of material disposed within a wall of the outer catheter member and/or the inner catheter member.

5. The catheter assembly as recited in claim 1, wherein the first distal end of the outer catheter member includes two or more segments of material, including a first segment and a second segment, the first segment comprising a different material than the second segment.

6. The catheter assembly as recited in claim 1, wherein the first distal end of the outer catheter member includes two or more segments of material, including a first segment and a second segment, the first segment having a different durometer than the second segment.

7. The catheter assembly as recited in claim 1, wherein relative movement between the first and second distal ends alters a shape of the first distal end of the outer catheter.

8. The catheter assembly as recited in claim 1, wherein the inner catheter member comprises a second lumen therein, the second lumen extending from the second distal end to the second proximal end.

9. The catheter assembly of claim 1 wherein the inner handle member includes a hemostasis mechanism.

10. The catheter assembly of claim 1 wherein at least a portion of the second distal end is extendable beyond the first distal end.

11. A catheter assembly comprising:

an outer catheter member extending from a first distal end to a first proximal end, where the first distal end is flexible;

the outer catheter member having a first lumen therein, the first lumen extending from the first distal end to the first proximal end, the outer catheter member further including an outer handle member coupled to the first proximal end;

a flexible inner catheter member movably disposed within the first lumen of the outer catheter member;

the inner catheter member extending from a second distal end to a second proximal end, the second distal end having a pre-formed curvature;

the inner catheter member having a second lumen therein, the second lumen extending from the second distal end to the second proximal end and including an inner handle member coupled to the second proximal end; and the first distal end of the outer catheter member includes two or more segments of material, including a first segment and a second segment, the first segment comprising a different material than the second segment, wherein the outer and inner catheter members are configured such that relative translation and rotation of the outer and inner catheter members causes the first distal end of the outer catheter member to assume a plurality of two and three dimensional shapes.

12. The catheter assembly as recited in claim 11, wherein the outer catheter member is more flexible than the inner catheter member.

13. The catheter assembly as recited in claim 11, wherein the outer catheter member has a preformed curve proximate to the first distal end.

14. The catheter assembly as recited in claim 11, further comprising a braid of material disposed between the outer catheter member and the inner catheter member.

15. The catheter assembly as recited in claim 11, further comprising a braid of material disposed within a wall of the outer catheter member and/or the inner catheter member.

16. The catheter assembly as recited in claim 11, further comprising a handle assembly including a sprocket and teeth configured to move the inner catheter member relative to the outer catheter member.

17. The catheter assembly of claim 11 wherein the inner handle member includes a hemostasis mechanism.

18. The catheter assembly of claim 11 wherein at least a portion of the second distal end is extendable beyond the first distal end.

\* \* \* \* \*